US012636105B2

(12) United States Patent
Mishra et al.

(10) Patent No.: US 12,636,105 B2
(45) Date of Patent: May 26, 2026

(54) SURGICAL ROBOTIC SYSTEMS INCLUDING SURGICAL ASSEMBLIES HAVING A SUPERCAPACITOR

(71) Applicant: Covidien LP, Mansfield, MA (US)

(72) Inventors: Ranjan K. Mishra, Orange, CT (US); Michael Zemlok, Prospect, CT (US)

(73) Assignee: Covidien LP, Mansfield, MA (US)

( * ) Notice: Subject to any disclaimer, the term of this patent is extended or adjusted under 35 U.S.C. 154(b) by 658 days.

(21) Appl. No.: 17/923,260

(22) PCT Filed: Jun. 17, 2021

(86) PCT No.: PCT/US2021/037719
§ 371 (c)(1),
(2) Date: Nov. 4, 2022

(87) PCT Pub. No.: WO2021/262510
PCT Pub. Date: Dec. 30, 2021

(65) Prior Publication Data
US 2023/0233277 A1　Jul. 27, 2023

Related U.S. Application Data

(60) Provisional application No. 63/043,241, filed on Jun. 24, 2020.

(51) Int. Cl.
| *A61B 34/37* | (2016.01) |
| *A61B 17/00* | (2006.01) |
| *H02P 3/18* | (2006.01) |

(52) U.S. Cl.
CPC .............. *A61B 34/37* (2016.02); *H02P 3/18* (2013.01); *A61B 2017/00017* (2013.01);
(Continued)

(58) Field of Classification Search
CPC .......... A61B 34/37; A61B 2017/00017; A61B 2017/00398; A61B 2017/00477;
(Continued)

(56) References Cited

U.S. PATENT DOCUMENTS

| 2016/0129598 A1 | 5/2016 | Geiler et al. |
| 2018/0079090 A1* | 3/2018 | Koenig ................... B25J 18/04 |
(Continued)

FOREIGN PATENT DOCUMENTS

| WO | 2017210516 A1 | 12/2017 |

OTHER PUBLICATIONS

International Search Report and Written Opinion dated Oct. 11, 2021, issued in corresponding international application No. PCT/US2021/037719, 11 pages.

*Primary Examiner* — Carl H Layno
*Assistant Examiner* — Dhrasti Snehal Dalal
(74) *Attorney, Agent, or Firm* — Carter, DeLuca & Farrell, LLP

(57) ABSTRACT

A surgical assembly for use with a robotic arm includes an outer housing configured to be selectively coupled to a robotic arm, a power pack disposed within the outer housing, and an electric motor operably coupled to the power pack. The outer housing has a supercapacitor attached to an inner surface of the outer housing. The power pack is configured to non-rotatably couple to a surgical instrument such that the surgical instrument and power pack are configured to rotate together. The supercapacitor is in electric communication with the electric motor and configured to supply a direct current to the electric motor to generate a braking torque during a power loss.

8 Claims, 6 Drawing Sheets

(52) U.S. Cl.
CPC .............. *A61B 2017/00398* (2013.01); *A61B 2017/00477* (2013.01); *A61B 2017/00734* (2013.01); *A61B 2017/00995* (2013.01)

(58) Field of Classification Search
CPC .......... A61B 2017/00734; A61B 2017/00995; A61B 34/35; A61B 2562/182; A61B 34/30; H02P 3/18
See application file for complete search history.

(56) References Cited

U.S. PATENT DOCUMENTS

| | | | |
|---|---|---|---|
| 2018/0347033 A1* | 12/2018 | Yoon ........................ | C23C 14/34 |
| 2019/0125458 A1* | 5/2019 | Shelton, IV ............. | A61B 5/00 |
| 2019/0201136 A1* | 7/2019 | Shelton, IV ........... | G16H 40/63 |
| 2020/0222727 A1* | 7/2020 | de Bruyn ............... | A61B 90/50 |

* cited by examiner

SURGICAL ROBOTIC SYSTEMS INCLUDING SURGICAL ASSEMBLIES HAVING A SUPERCAPACITOR

FIELD

The present technology is generally related to surgical robotic systems used in minimally invasive medical procedures.

BACKGROUND

Some surgical robotic systems included a console supporting a surgical robotic arm and a surgical instrument or at least one end effector (e.g., forceps or a grasping tool) mounted to the robotic arm. The robotic arm provided mechanical power to the surgical instrument for its operation and movement. Each robotic arm may have included an instrument drive unit operatively connected to the surgical instrument. The instrument drive unit had one or more electric motors configured to mechanically drive one or more components of the surgical instrument.

SUMMARY

In accordance with an aspect of the present disclosure, a surgical assembly for use with a robotic arm is provided. The surgical assembly includes an outer housing configured to be selectively coupled to a robotic arm, a power pack disposed within the outer housing, and an electric motor operably coupled to the power pack. The outer housing has a supercapacitor attached to an inner surface of the outer housing. The power pack is rotatable relative to the outer housing and configured to non-rotatably couple to a surgical instrument such that the surgical instrument and power pack are configured to rotate together. The electric motor is configured to effect the rotation of the power pack. The supercapacitor is in electric communication with the electric motor and configured to supply a direct current to the electric motor to generate a braking torque.

In aspects, the supercapacitor may be a thin-film graphene supercapacitor coated on the inner surface of the outer housing.

In aspects, the outer housing may further include a faraday cage attached to the inner surface of the outer housing.

In aspects, the surgical assembly may further include a printed circuit board associated with the electric motor and configured to control power to the electric motor.

In aspects, the supercapacitor may have contact terminals configured to electrically couple with the printed circuit board.

In aspects, the electric motor may include a rotor, and motor windings in communication with the supercapacitor. The supercapacitor may be configured to induce power to the motor windings to activate a phase lock of the electric motor for a fixed duration of time.

In accordance with another aspect of the disclosure, a surgical robotic system is provided. The surgical robotic system includes an IDU holder and an instrument drive unit. The IDU holder includes a carriage configured to be slidably supported on a robotic arm, an electric motor supported in the carriage, and a printed circuit board associated with the electric motor and configured to control power to the electric motor. The instrument drive unit includes an outer housing configured to be selectively coupled to the carriage of the IDU holder, and a power pack disposed within the outer housing. The outer housing has a supercapacitor attached to an inner surface of the outer housing. The power pack is rotatable relative to the outer housing and operably coupled to the electric motor. The power pack is configured to be rotated by the electric motor. The supercapacitor is in electric communication with the electric motor and configured to supply a direct current to the electric motor to generate a braking torque.

In aspects, the surgical robotic system may further include an electromechanical surgical instrument defining a longitudinal axis. The electromechanical surgical instrument may be configured to be non-rotatably coupled to the power pack such that the electromechanical surgical instrument rotates about the longitudinal axis with a rotation of the power pack.

Further details and aspects of exemplary embodiments of the present disclosure are described in more detail below with reference to the appended figures.

BRIEF DESCRIPTION OF THE DRAWINGS

Embodiments of the present disclosure are described herein with reference to the accompanying drawings, wherein.

DETAILED DESCRIPTION

Figure 1:
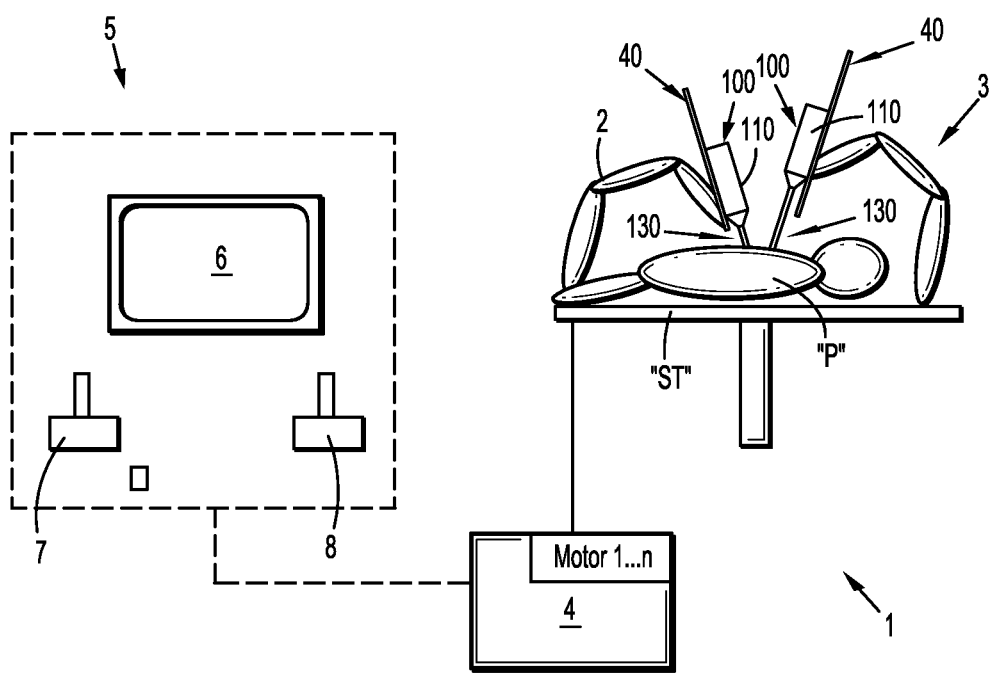
FIG. 1 is a schematic illustration of a surgical robotic system including a surgical robotic assembly in accordance with the present disclosure.

Embodiments of the presently disclosed surgical robotic system and methods thereof are described in detail with reference to the drawings, in which like reference numerals designate identical or corresponding elements in each of the several views. As used herein the term "distal" refers to that portion of the surgical robotic system that is closest to the patient, while the term "proximal" refers to that portion of the surgical robotic system further from the patient.

The present disclosure is directed to a means or system for automatically braking an electric motor in a surgical robotic system during a power loss. The instrument drive unit of the surgical robotic system includes a supercapacitor, such as, for example, a stack of super/ultra capacitors or a custom designed thin film graphene supercapacitor. The graphene supercapacitor may be applied to an inner surface of the enclosure or outer shell housing of the instrument drive unit. The enclosure has a vacuum-deposited copper with aluminum coating on the inside surface to create a faraday cage. The thin film graphene super capacitor may be suitably deposited in addition to the faraday cage layer with an insulation layer(s). The enclosure has contact pads from the supercapacitor terminals and are connected to respective targets on an inner shell housing of the instrument drive unit to close the circuit when assembled.

During regular use when the instrument drive unit is powered, the supercapacitor is charged through a charging circuit. When power to the instrument drive unit is off (or in the event of a power failure), the now-charged supercapacitor induces power to motor windings to activate a phase lock for a fixed duration of time. Additionally, the instrument drive unit may have a rechargeable/replaceable battery with required capacity for longer duration phase induced locking.

Applying a small DC voltage, by the supercapacitor, to one or all phases of a brushless DC electric motor holds the rotor as a brake. The winding current, which is proportional to motor torque, defines the holding torque. Overall performance of this type of holding brake depends on the required amount of holding torque and a total duration of holding. For the brake mechanism of the present disclosure, a limited amount of power is available for a limited period of time. Therefore, with the power-off/no-source-power electrically-activated-braking-option, the two parameters of power and time define the specifications of the energy storing device. An electrical current is supplied from an energy storing device (e.g., the supercapacitor) for a targeted holding torque, a pre-calculated voltage for a pre-estimated period of time. Other features and benefits of the disclosed surgical assemblies are further detailed below.

Figure 2:
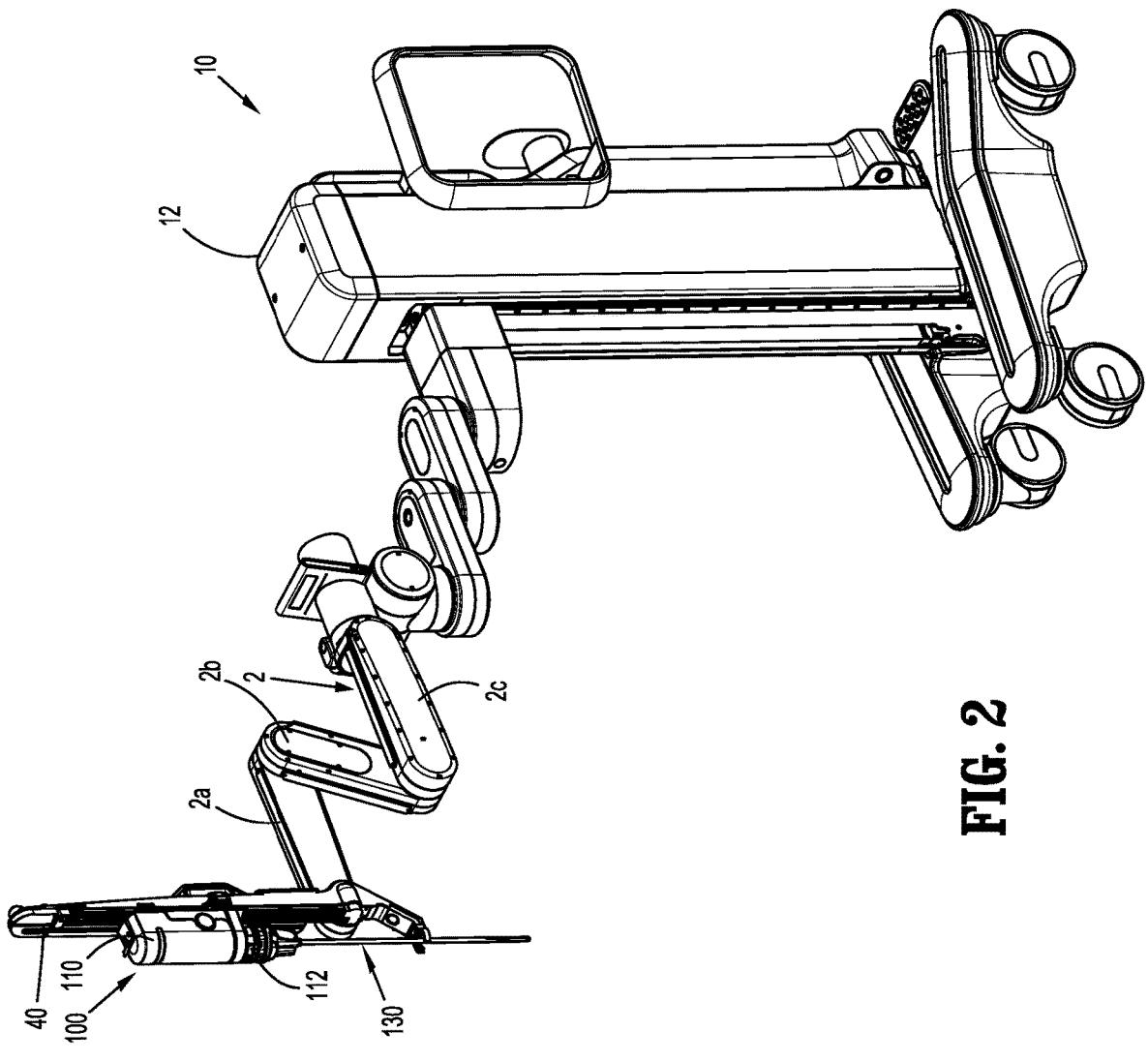
FIG. 2 is a perspective view of the surgical robotic assembly of FIG. 1 attached to a robotic arm, which is attached to a robotic arm cart.

Referring to FIGS. 1 and 2, a surgical system, such as, for example, a surgical robotic system 1, generally includes a robotic arm or robotic arms 2, 3 coupled to a robotic cart 10, and a surgical assembly 100 coupled to the surgical robotic arm 2. The surgical assembly 100 includes an instrument drive unit 110 (hereinafter "IDU 110") coupled to a slide rail 40 of surgical robotic arms 2, 3, and an electromechanical surgical instrument 130 operably coupled to IDU 110 by a sterile interface module 112 of surgical assembly 100.

The surgical system 1 further includes a control device 4 and an operating console 5 coupled with control device 4. Operating console 5 includes a display device 6, which is set up in particular to display three-dimensional images; and manual input devices 7, 8, by means of which a person (not shown), for example a surgeon, is able to telemanipulate robotic arms 2, 3 in a first operating mode, as known in principle to a person skilled in the art. Each of the robotic arms 2, 3 may be composed of a plurality of members 2a, 2b, 2c, which are connected through joints. Robotic arms 2, 3 may be driven by electric drives (e.g., motors, not shown) that are connected to control device 4. Control device 4 (e.g., a computer) may be set up to activate the drives, in particular by means of a computer program, in such a way that robotic arms 2, 3, the attached surgical robotic assembly 100, and thus electromechanical surgical instrument 130 (including an electromechanical end effector (not shown)) execute a desired movement according to a movement defined by means of manual input devices 7, 8. Control device 4 may also be set up in such a way that it regulates the movement of robotic arms 2, 3.

Surgical robotic system 1 is configured for use on a patient "P" lying on a surgical table "ST" to be treated in a minimally invasive manner by means of a surgical instrument, e.g., electromechanical surgical instrument 130. In embodiments, robotic arms 2, 3 may be coupled to robotic arm cart 10 (FIG. 2) rather than surgical table "ST." Surgical robotic system 1 may also include more than two robotic arms 2, 3, the additional robotic arms likewise being connected to control device 4 and being telemanipulatable by means of operating console 5. A surgical instrument, for example, electromechanical surgical instrument 130 (including the electromechanical end effector), may also be attached to the additional robotic arm.

Control device 4 may control a plurality of motors, e.g., motors (Motor 1 . . . n), with each motor configured to drive movement of robotic arms 2, 3 in a plurality of directions. Further, control device 4 may control a power pack 114 (FIGS. 3-4) of IDU 110 of surgical robotic assembly 100 that drives various operations of surgical instrument 130. In addition, control device 4 may control the operation of a rotation motor, such as, for example, a brushless DC electric motor "M" (FIG. 4) of IDU 110 of surgical assembly 100, configured to drive a relative rotation of power pack 114 of IDU 110 and in turn, sterile interface module 112, and electromechanical surgical instrument 130. In embodiments, each motor 114 of the IDU 110 can be configured to actuate a drive rod/cable or a lever arm to effect operation and/or movement of electromechanical surgical instrument 130.

For a detailed discussion of the construction and operation of a surgical robotic system, reference may be made to U.S. Pat. No. 8,828,023, entitled "Medical Workstation," the entire contents of which are incorporated by reference herein.

Figure 3:
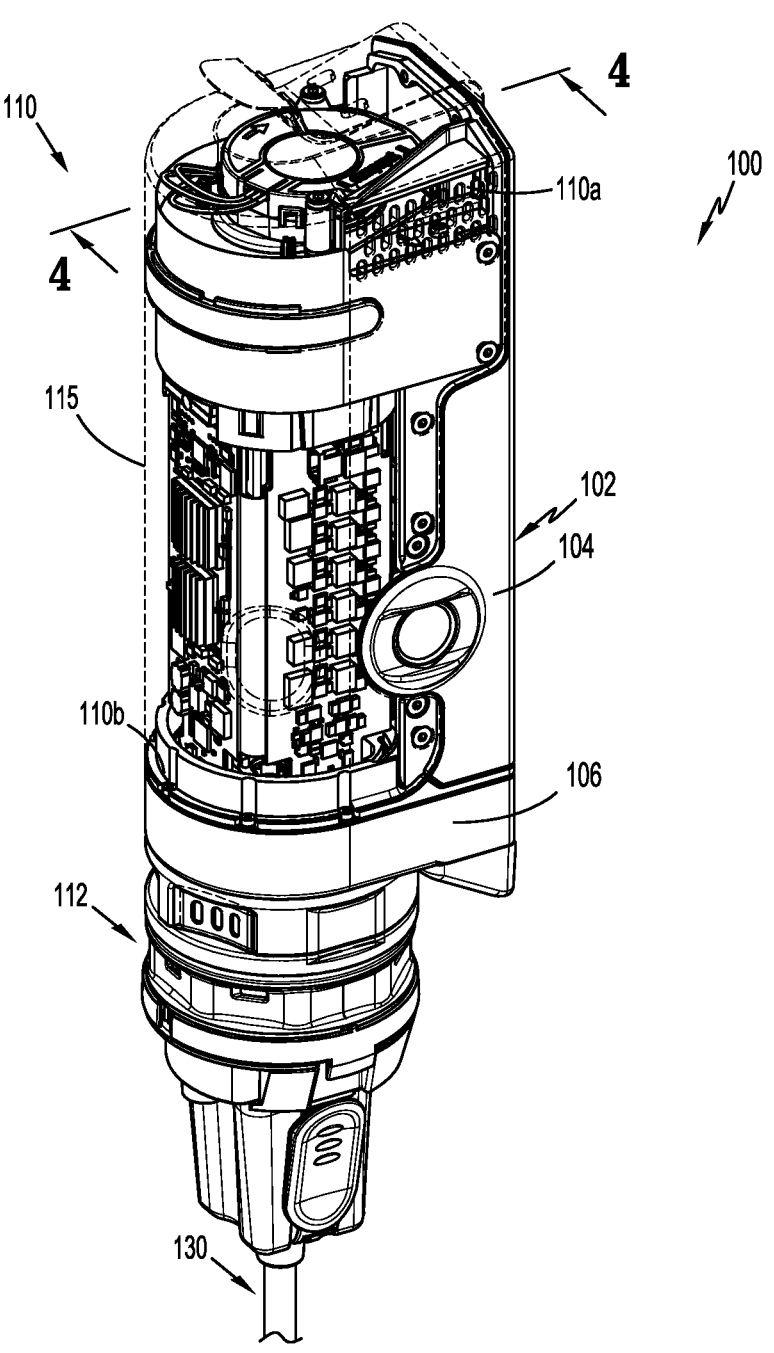
FIG. 3 is a perspective view of the surgical robotic assembly of FIG. 2 including an IDU holder, an instrument drive unit supported on the IDU holder, and a surgical instrument coupled to the instrument drive unit.
Figure 4:
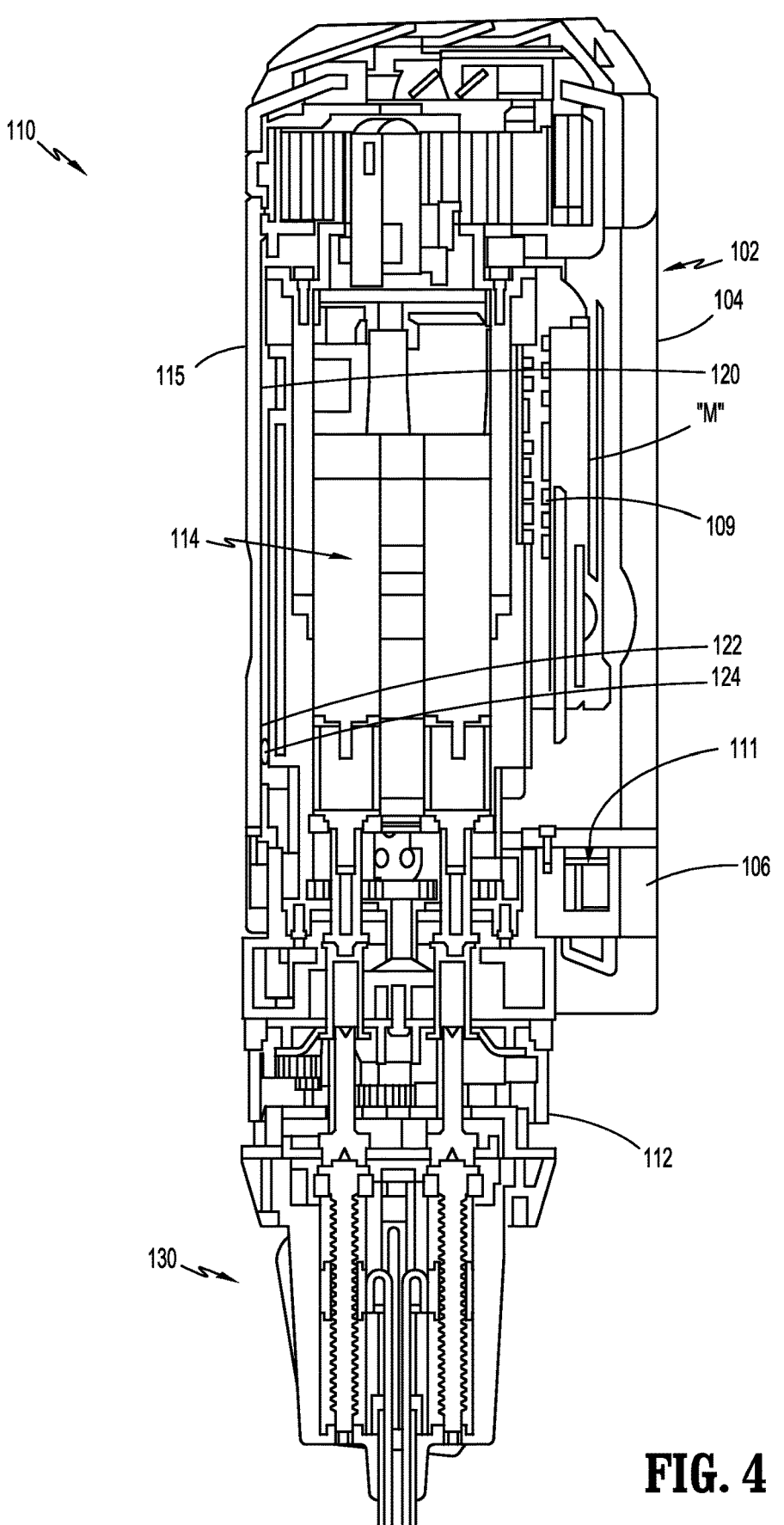
FIG. 4 is a cross-sectional view, taken alone line 4-4 in FIG. 3, illustrating internal components of the instrument drive unit and IDU holder.

With reference to FIGS. 3 and 4, surgical assembly 100 of surgical system 1, which is configured to be coupled with or to robotic arm 2 or 3, generally includes the IDU holder 102, the IDU 110, and the electromechanical surgical instrument 130. As briefly mentioned above, IDU 110 transfers power and actuation forces from its motors (e.g., power pack 114) to driven members (not shown) of electromechanical surgical instrument 130 to ultimately drive movement of components of the end effector of electromechanical surgical instrument 130, for example, a movement of a knife blade (not shown) and/or a closing and opening of jaw members of the end effector, the actuation or firing of a stapler, and/or the activation or firing of an electrosurgical energy-based instrument, or the like.

IDU holder 102 of surgical assembly 100 functions both to actuate a rotation of power pack 114 of IDU 110 and to effect axial translation of IDU 110 along rail 40 of robotic arm 2. IDU holder 102 includes a back member or carriage 104, and an outer member or outer housing 106 extending laterally (e.g., perpendicularly) from a distal end of carriage 104. In some aspects, housing 106 may extend at various angles relative to carriage 104 and from various portions of carriage 104. Carriage 104 has a rear side detachably connectable to rail 40 (FIG. 2) of robotic arm 2 to enable IDU holder 102 to slide or translate along rail 40 of robotic arm 2. A front side of carriage 104 is configured to support an outer housing 115 of the IDU 110.

Carriage 104 of IDU holder 102 supports or houses a motor, such as, for example, a canister motor "M" therein. Motor "M" receives controls and power from control device 4 (FIG. 1) to ultimately rotate internal power pack 114 of IDU 110. Carriage 104 includes a printed circuit board 109 in electrical communication with motor "M" of carriage 104 to control an operation of motor "M" of carriage 104. Carriage 104 further includes a belt or gear drive mechanism 111 that extends distally from motor "M." Drive mechanism 111 is configured to operably interface with power pack 114 of IDU 110 to effect a rotation of power pack 114 upon actuation of motor "M" of carriage 104.

The motor "M" may be disposed in a distal end 110b of the IDU 110 and laterally adjacent the power pack 114. The motor "M" is a three-phase brushless DC motor having an outer stator (not explicitly shown) having a plurality of motor windings "W" (FIG. 7) and an inner rotor "R" (FIG.

7) having a pair of permanent magnets (not explicitly shown). In aspects, the electric motor "M" may be any suitable electric motor, such as, for example, a single-phase, two-phase, or three-phase AC permanent magnet (PM) motor or any suitable type of DC PM motor. Printed circuit board 109 may have a controller associated with the motor "M" for governing the speed and direction of rotation of the rotor "R" of the electric motor "M."

For a more detailed description of an IDU having a canister motor and its overall operation, reference may be made to U.S. Patent Application Publication No. 2019/0133703, filed on Jun. 2, 2017, the entire contents of which being incorporated by reference herein.

Figure 5:
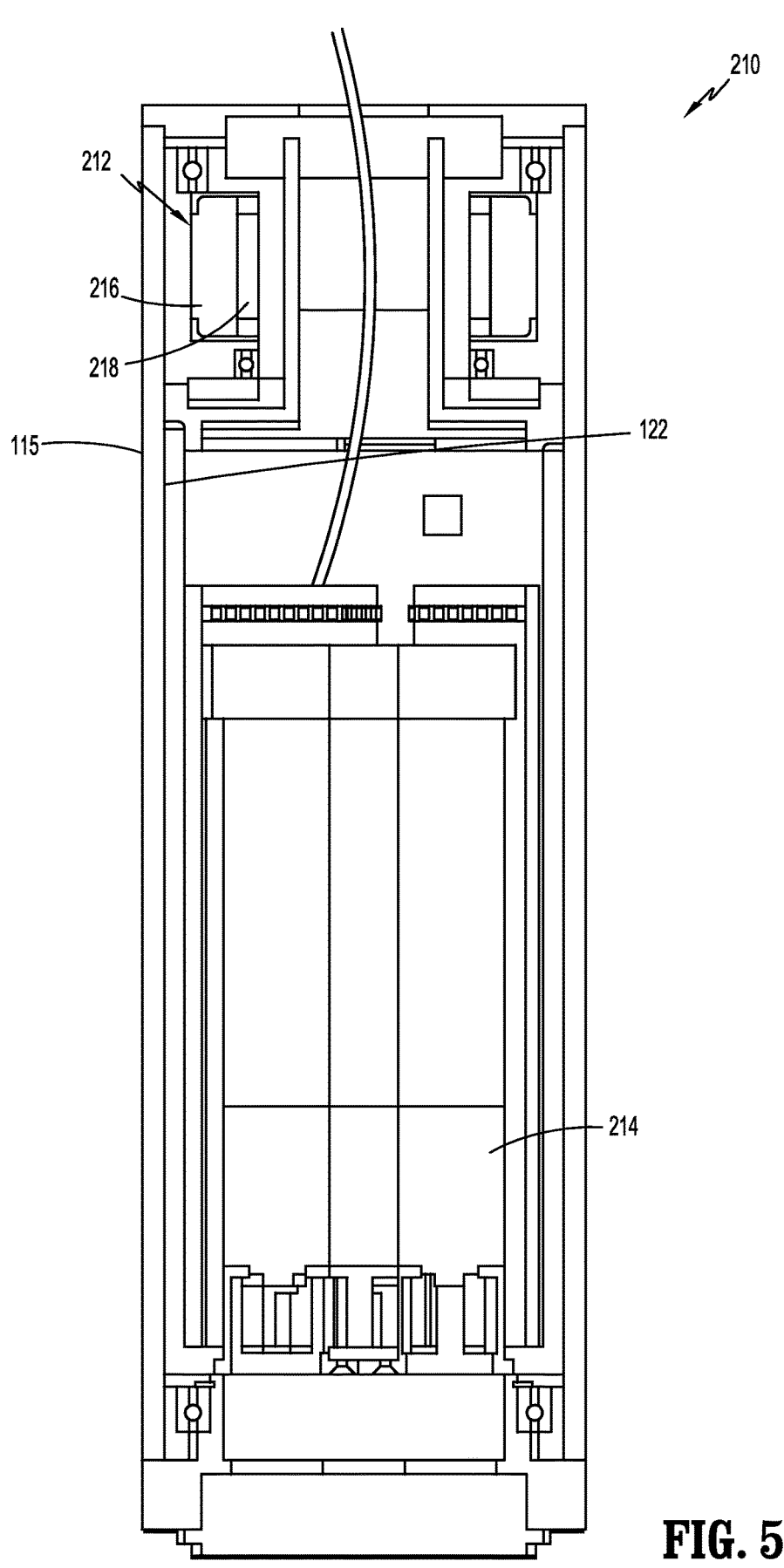
FIG. 5 is a cross-sectional view illustrating another embodiment of an instrument drive unit of the surgical robotic assembly of FIG. 1.

With brief reference to FIG. 5, in another aspect of the disclosure, instead of an IDU 110 having a motor "M" being a canister motor disposed laterally adjacent a power pack 114, an IDU 210 is provided that includes a hollow core, three-phase brushless DC motor 212 disposed in a proximal end of IDU 210 and above the power pack 214. Motor 212 includes an outer stator 216 and an inner rotor 218 non-rotatably coupled to motor pack 214.

For a more detailed description of an IDU with a hollow core motor and its overall operation, reference may be made to U.S. Patent Application Publication No. 2018/0168748, filed on Jun. 15, 2016, the entire contents of which being incorporated by reference herein.

Figure 6:
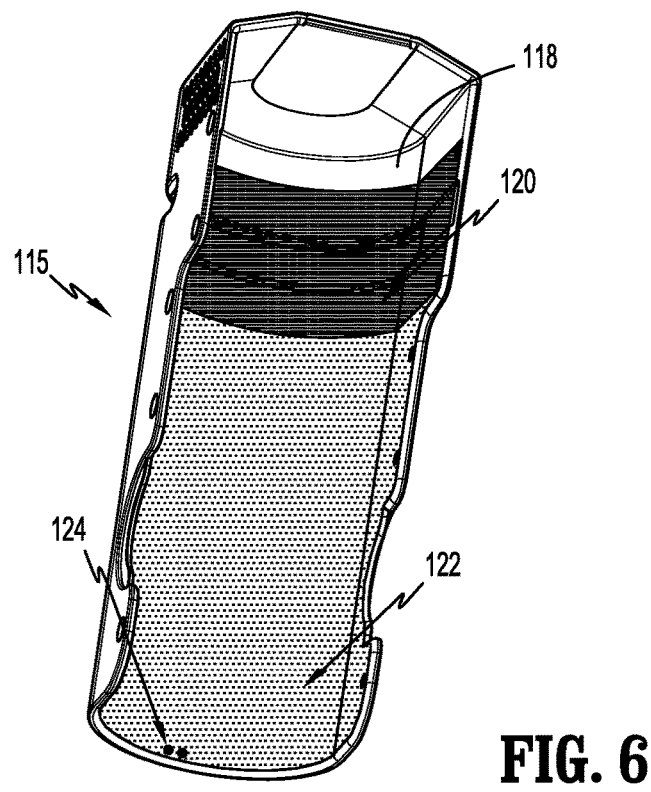
FIG. 6 is a perspective view of an outer housing of the instrument drive unit of FIG. 3.

With continued reference to FIGS. 4 and 6, the outer housing or enclosure 115 of IDU 110 is engaged to the front side of carriage 104 of IDU holder 102 so as to shroud, cover and protect the inner components of IDU 110 and carriage 104. The housing 104 may form a sterile barrier between an interior of instrument drive unit 100 and the external environment to shield various components of IDU 110 that are responsible for transferring power and data to components of IDU 110. The housing 115 may be disposable, re-usable (upon sterilization), and/or transparent. Housing 115 of IDU 110 may have a generally cylindrical configuration, but in some embodiments, housing 115 may assume a variety of configurations, such as, for example, squared, triangular, elongate, curved, semi-cylindrical or the like.

The housing 115 of IDU 110 has an inner surface 118 on which copper with aluminum is vacuum-deposited, thereby forming a faraday cage 120 to protect certain electrical components within IDU 110 from external electromagnetic fields. The inner surface 118 further includes a thin-film graphene supercapacitor 122 deposited thereon. In aspects, the supercapacitor 122 may be deposited on a separate section of inner surface 118 of housing 115 or deposited over the faraday cage 120 with a layer of insulative material disposed therebetween. In aspects, the supercapacitor 122 may be any suitable type of supercapacitor, such as, for example, a stack of electrostatic double-layer supercapacitors or a rechargeable battery packaged inside of the instrument drive unit 110. In other aspects, a conventional capacitor may be implemented. The supercapacitor 122 has a pair of terminals 124 configured to contact a corresponding pair of contact targets of the printed circuit board 109 of the IDU 110 upon assembling the IDU 110. Therefore, upon enclosing the internal components of IDU 110 within the housing 115, the supercapacitor 122 is in electrical communication with the motor "M" via the printed circuit board 109.

Figure 7:
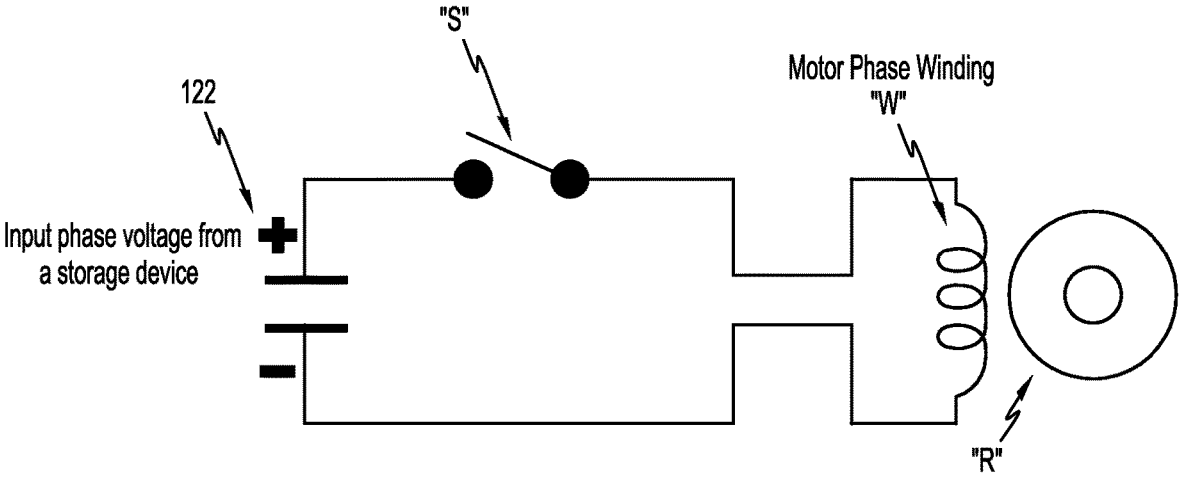
FIG. 7 is a schematic diagram of an electronic circuit of the surgical assembly of FIG. 3.

FIG. 7 illustrates a schematic diagram of certain features of an electric circuit formed between the supercapacitor 122 and the motor "M." In particular, the circuit includes a storage device, such as, for example, the supercapacitor 122, a switch "S," and a motor phase winding "W" of the motor "M." During normal operation (e.g., when power is supplied to the motor "M"), the switch "S" is open, whereby the supercapacitor 122 is charged by a charging circuit (not explicitly shown) that is in electric communication with an external power source or an internal battery source (e.g., a battery).

During a power loss, the controller of the printed circuit board 109 closes the switch "S," whereby the stored energy in the supercapacitor 122 induces power (e.g., sends an electric current) to the motor phase winding "W" of the "M" to activate a phase lock for a fixed duration of time. As such, motor "M" generates a braking torque on the inner rotor "R" to stop and/or prevent further rotation of the power pack 114 and the attached sterile interface module 112 (FIG. 3).

In aspects, the IDU 110 may have a rechargeable/replaceable battery with required capacity for longer duration induced locking.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

It will be understood that various modifications may be made to the embodiments disclosed herein. Therefore, the above description should not be construed as limiting, but merely as exemplifications of various embodiments. Those skilled in the art will envision other modifications within the scope and spirit of the claims appended thereto.

The invention claimed is:

1. A surgical assembly for use with a robotic arm, the surgical assembly comprising:
an outer housing configured to be selectively coupled to a robotic arm, the outer housing having a supercapacitor attached to an inner surface of the outer housing, wherein the supercapacitor is a thin-film graphene supercapacitor coated on the inner surface of the outer housing, wherein the outer housing further includes a faraday cage attached to the inner surface of the outer housing, and wherein the supercapacitor is deposited over the faraday cage;

a power pack disposed within the outer housing and rotatable relative to the outer housing, the power pack configured to non-rotatably couple to a surgical instrument such that the surgical instrument and power pack are configured to rotate together, wherein the power pack drives functionality of the surgical instrument, and wherein the super capacitor is disposed between the outer housing and the power pack; and an electric motor disposed within the housing and operably coupled to the power pack and configured to affect the rotation of the power pack relative to the outer housing, wherein the supercapacitor is in electric communication with the electric motor and configured to supply a direct current to the electric motor to generate a braking torque.

2. The surgical assembly according to claim 1, further comprising a printed circuit board associated with the electric motor and configured to control power to the electric motor.

3. The surgical assembly according to claim 2, wherein the supercapacitor has contact terminals configured to electrically couple with the printed circuit board.

4. The surgical assembly according to claim 3, wherein the electric motor includes a rotor, and motor windings in communication with the supercapacitor, the supercapacitor configured to induce power to the motor windings to activate a phase lock of the electric motor for a fixed duration of time.

5. An instrument drive unit for use with a robotic arm, the instrument drive unit comprising:

a housing having a supercapacitor attached to a surface of the housing, wherein the supercapacitor is a thin-film graphene supercapacitor coated on an inner surface of the housing, wherein the housing further includes a faraday cage attached to the inner surface of the housing, and wherein the supercapacitor is deposited over the faraday cage;

a power pack disposed within the housing and rotatable relative to the housing, the power pack configured to non-rotatably couple to a surgical instrument such that the surgical instrument and power pack are configured to rotate together, wherein the power pack drives functionality of the surgical instrument, and wherein the super capacitor is disposed between the housing and the power pack; and an electric motor disposed within the housing and operably coupled to the power pack, the electric motor configured to rotate the power pack relative to the housing, wherein the supercapacitor is in electric communication with the electric motor and configured to supply a direct current to the electric motor to generate a braking torque, wherein, when the braking torque is generated, rotation of the power pack is prevented.

6. The instrument drive unit according to claim 5, further comprising a printed circuit board associated with the electric motor, the printed circuit board configured to control power to the electric motor.

7. The instrument drive unit according to claim 6, wherein the supercapacitor has contact terminals configured to electrically couple with the printed circuit board.

8. The instrument drive unit according to claim 7, wherein the electric motor includes:

a rotor; and motor windings in communication with the supercapacitor, wherein the supercapacitor is configured to induce power to the motor windings to activate a phase lock of the electric motor for a fixed duration of time.

* * * * *